United States Patent [19]

Nichols

[11] Patent Number: 5,183,643

[45] Date of Patent: * Feb. 2, 1993

[54] MEDICAL INSTRUMENT STERILIZATION CONTAINER

[76] Inventor: Robert L. Nichols, 4555 N. Jackson, Jacksonville, Tex. 75766

[*] Notice: The portion of the term of this patent subsequent to Mar. 1, 2005 has been disclaimed.

[21] Appl. No.: 762,060

[22] Filed: Sep. 17, 1991

Related U.S. Application Data

[60] Continuation of Ser. No. 477,594, Feb. 9, 1990, abandoned, which is a continuation of Ser. No. 335,361, Apr. 10, 1989, Pat. No. 4,900,519, which is a continuation of Ser. No. 208,730, Jun. 17, 1988, Pat. No. 4,915,918, which is a continuation of Ser. No. 821,136, Jan. 22, 1986, Pat. No. 4,752,453, which is a division of Ser. No. 668,090, Nov. 5, 1984, Pat. No. 4,617,178.

[51] Int. Cl.$^5$ .............................................. A61L 2/26
[52] U.S. Cl. ..................................... 422/297; 206/363; 206/439; 422/300; 422/310
[58] Field of Search ............... 422/292, 294, 297, 300, 422/310; 206/363, 439

[56] References Cited

U.S. PATENT DOCUMENTS

| | | | |
|---|---|---|---|
| 2,342,067 | 2/1944 | Turner | 422/300 |
| 3,410,395 | 11/1968 | Sellers | 229/3.5 MF |
| 3,437,423 | 4/1969 | Mondiadis . | |
| 3,454,189 | 7/1969 | Lauterbach . | |
| 3,697,223 | 10/1972 | Kovalcik et al. . | |
| 3,750,827 | 8/1973 | Wick | 229/3.5 MF |
| 3,890,096 | 6/1975 | Nichol et al. . | |
| 3,946,872 | 3/1976 | Sturm | 229/3.5 MF |
| 4,105,407 | 8/1978 | Sanderson . | |
| 4,121,714 | 10/1978 | Daly et al. | 422/119 |
| 4,124,141 | 11/1978 | Armentrout et al. . | |
| 4,154,342 | 5/1979 | Wallace . | |
| 4,196,166 | 4/1980 | Sanderson . | |
| 4,210,674 | 7/1980 | Mitchell | 229/3.5 MF |
| 4,251,482 | 2/1981 | Sanderson et al. . | |
| 4,267,420 | 5/1981 | Brastad | 229/3.5 MF |
| 4,359,495 | 11/1982 | Schroeder et al. | 229/3.5 MF |
| 4,372,921 | 2/1983 | Sanderson et al. . | |
| 4,402,407 | 9/1983 | Maly . | |
| 4,416,417 | 11/1983 | Sanderson et al. . | |
| 4,416,907 | 11/1983 | Watkins | 229/3.5 MF |
| 4,458,705 | 7/1984 | Cawood . | |
| 4,512,498 | 4/1985 | Leibinger . | |
| 4,551,311 | 11/1985 | Lorenz | 422/300 |
| 4,704,254 | 11/1987 | Nichols | 422/310 X |
| 4,728,504 | 3/1988 | Nichols | 422/310 X |
| 4,752,453 | 6/1988 | Nichols | 422/310 X |
| 4,915,918 | 4/1990 | Nichols | 422/300 X |

FOREIGN PATENT DOCUMENTS 2542200 9/1984 France .
2165754 4/1986 UK .

Primary Examiner—Jill A. Johnston
Attorney, Agent, or Firm—Baker & Botts

[57] ABSTRACT

A medical instruments sterilization container (10) includes a housing (12) and a removable lid (14). A removable tray (16) is adapted to hold various medical instruments to be sterilized. The container is formed of a polymer of relatively low thermal conductivity, with a material having a relatively high thermal conductivity being added thereto in order to substantially increase the overall thermal conductivity of the container to absorb radiant heat and rapidly conduct that heat throughout the container to reduce condensate within the container.

3 Claims, 2 Drawing Sheets

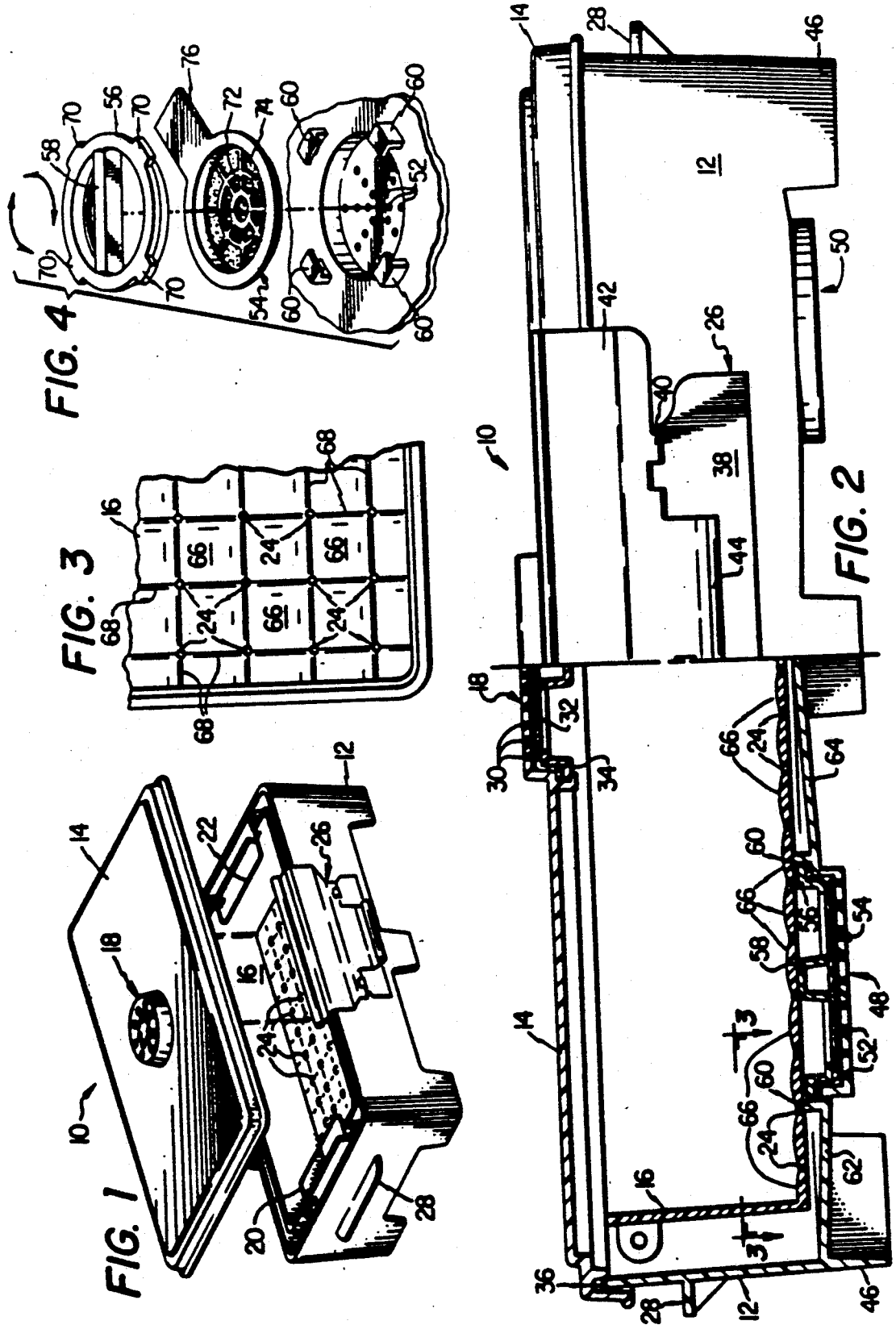

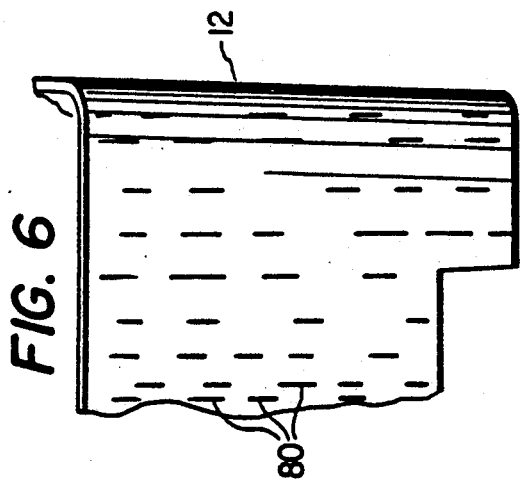
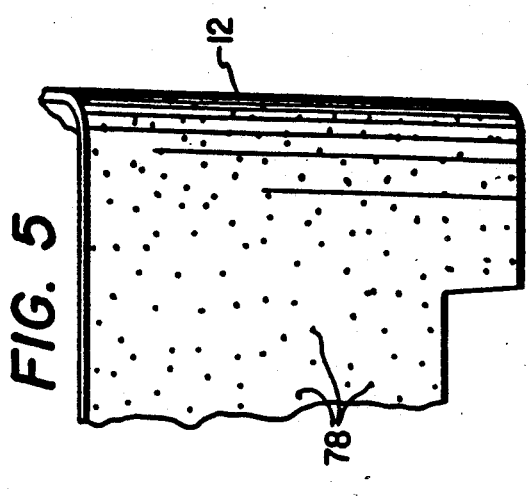
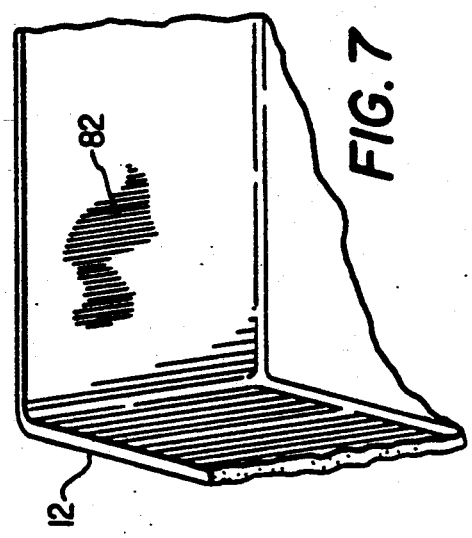

MEDICAL INSTRUMENT STERILIZATION CONTAINER

RELATED APPLICATIONS

This is a continuation of U.S. patent application Ser. No. 07/477,594, filed Feb. 9, 1990, now abandoned, which in turn is a continuation of U.S. patent application Ser. No. 07/335,361, filed Apr. 10, 1989, now U.S. Pat. No. 4,900,519, which in turn is a continuation of U.S. patent application Ser. No. 07/208,730, filed Jun. 17, 1988, now U.S. Pat. No. 4,915,918, which in turn is a continuation of U.S. patent applicaiton Ser. No. 06/821,136, filed Jan. 22, 1986, now U.S. Pat. No. 4,752,453, which in turn is a division of U.S. patent application Ser. No. 06/668,090, filed Nov. 5, 1984, now U.S. Pat. No. 4,617,178.

TECHNICAL FIELD OF THE INVENTION

This invention relates to sterile containers and more particularly relates to a medical instrument sterilization container with an offset filter.

BACKGROUND OF THE INVENTION

It is necessary in hospital and other medical environments to sterilize medical instruments with steam or ethylene oxide. Various types of sterilization containers for such medical instruments have heretofore comprised muslin wraps, various paper wraps and sterilization containers. When using the various types of wraps, medical instruments are placed in a tray, wrapped by a recommended procedure, taped, labeled and placed in a steam or ethylene oxide sterilizer. The steam or ethylene oxide penetrates the wrap and kills the bacteria. Disadvantages in the use of the sterilization wraps include the repeated expenses of the disposable wraps, potential punctures of wrapping materials thereby causing contamination, limited shelf life of the wrapped instruments and the fact that the wraps are not stackable.

Various sterilization containers have been heretofore proposed which provide a hermetically sealed container with various filters which provide a relatively long shelf life, which cannot be easily punctured, which enable improved organization of the medical instruments and which are stackable. Sterilization containers made of metal, such as stainless steel and aluminum, have been used, but are relatively expensive. These devices are generally also opaque, thereby preventing a visual inventory of the container interiors. Consequently, sterilization containers made of plastics have been developed which can withstand the harsh environments of the sterilization chamber and which are clear such that inventories of the containers can be seen. Examples of such previously developed plastic sterilization containers are the Sterile-Case system manufactured and sold by Bemis Corporation and the Steri-Stor system manufactured and sold by Research Surgical Systems of Santa Ana, California.

Prior plastic sterilization containers have, however, suffered from the problem of condensate accumulation on the internal and external surfaces after sterilization. Although bacteria inside the container should be substantially eliminated through the sterilization process, medical technicians are trained to regard moisture as a breeding place for bacteria and thus condensate tends to cause technician acceptance problems, as well as providing an actual possible breeding ground for bacteria. In addition, the condensate increases the possibility for rusting and other deterioration of the metal instruments in the container.

Steam sterilization units, whether they be gravity steam, pulsating pressure steam or alternating vacuum and pressure or the like, all normally have a drying cycle. During the drying cycle, steam is applied to the jacket of the autoclave to create a hot environment and normally some vacuum is applied to the chamber in order to lower the boiling point of the moisture. The drying cycle is utilized to evaporate the moisture in the sterilization container wrap or the like. However, clear or translucent plastic sterilization containers have a relatively low thermal conductivity and thus do not allow the residual moisture to be evaporated within an economical time frame. The heat reaching the sterilization container within the sterilization unit comprises both conductive and radiated heat. The conductive heat tends to heat the container relatively slowly, in turn heating the moisture in the container and creating slow evaporation. The radiated heat emanates from the jacket of the autoclave, but such radiant heat is not able to be utilized in evaporation of clear or translucent plastic containers because the majority of the radiative heat passes through the clear surface of the plastic containers. The need has thus arisen for a plastic sterilization container which enables the sterilization of medical instruments and which also tends to prevent or eliminate condensate from being formed on the interior surfaces thereof within an economical time frame.

SUMMARY OF THE INVENTION

In accordance with the present invention, a medical instrument sterilization container comprises a housing dimensioned to receive medical instruments for sterilization by gas or steam. A removable lid for the housing enables access to the housing and seals with the housing to maintain the sterility of the housing interior. The housing is formed from a polymer of relatively low thermal conductivity and also includes material having relatively high thermal conductivity in order that the housing absorbs radiant heat to reduce condensate within the container. The high thermal conductivity material may be mixed in the polymer or may be painted or coated on the container.

In accordance with another aspect of the invention, a medical instrument sterilization container includes a housing having a bottom and side walls for receiving medical instruments for sterilization. A removable lid having an aperture therethrough sealingly fits over the housing. A housing bottom slopes to at least one location to bring condensate to the one location. A filter is disposed in the aperture and the housing bottom at the one location. The filters passes air therethrough but prevents passage of contaminants into the housing.

In accordance with yet another aspect of the invention a medical instrument sterilization container includes a housing for receiving medical instruments for sterilization. A removable lid sealingly fits over the housing. A tray is removably disposed within the housing for supporting the medical instruments. Apertures are formed through the bottom of the tray to drain condensate therefrom. The tray has domed portions between the apertures in order to facilitate draining of condensate.

BRIEF DESCRIPTION OF THE DRAWINGS

For a more complete understanding of the present invention and the objects and advantages thereof, reference is now made to the following description taken in conjunction with the accompanying Drawings in which:

FIG. 1 is a perspective view of the present sterilization container showing the lid in an exploded position;

FIG. 2 is a partially sectioned view of one-half of the length of the present sterilization container in conjunction with a front elevation thereof;

FIG. 3 is a top sectional view of a portion of the bottom of the removable tray of the invention taken along section lines 3—3 in FIG. 2;

FIG. 4 is an exploded view of one of the removable filters of the invention;

FIG. 5 is a partial view of the housing showing the mixture of high thermal conductivity material within the clear plastic;

FIG. 6 is a partial view of the housing showing the high conductivity fibers mixed within the plastic; and FIG. 7 is a partial view of the housing showing a high thermal conductivity material painted onto the inside surface thereof.

DETAILED DESCRIPTION OF THE INVENTION

Referring to FIG. 1, the present sterilization container is identified generally by the numeral 10 and may be seen to include the housing 12 and a removable lid 14. A removable tray 16 is received within the housing 12 and is adapted to receive various medical instruments such as knives, scissors and the like.

A filter 18 is disposed through the lid 14 in order to allow the passage of heated sterile air or other sterilizing gases therethrough while preventing the passage of bacteria or other contaminants into the interior of the container. Two additional filters, to be subsequently described, are disposed in the bottom of the housing 12. The tray 16 includes removable metal handles 20 and 22 to enable easy withdrawal of the tray 16 from the housing 12. Apertures 24 are disposed through the tray 16 to allow the passage of steam and condensate therethrough. Metal clamps 26 are attached on both sides of the housing 12 and are manually movable in order to clamp against the side of the lid 14 in order to lock the lid to the housing. Suitable sealing surfaces are provided between the housing 12 and the lid 14 in order to provide an essentially airtight container when the lid is clamped to the housing. Handles 28 are provided on opposite ends of container 12 to facilitate handling.

FIG. 2 illustrates a partially sectioned view of the sterilization container of the present invention. The filter 18 may be seen to include apertures 30 which communicate with the atmosphere. A removable filter 32 is clamped into place by a twistable cap 34. A sealing portion 36 is illustrated between the housing 12 and the lid 14. The clamps 26 may be seen to comprise a stationary portion 38 which is pivotally mounted by pivot 40 to a pivotal clamp portion 42. Manual depression upon a lip 44 causes clamp 42 to be moved outwardly in order to accept the lid 14. When the lid 14 is in place, the movable clamp member 42 is moved by spring pressure to clamp against the lid in order to sealingly affix it to the housing.

FIG. 2 further illustrates pedestals 46 which elevate the bottom of the housing 12. Also disposed on the bottom of the housing 12 are two additional filters 48 and 50 which are constructed in a similar manner as filter 18. Apertures 52 are disposed through the bottom of the housing 12 in the filter area. A removable filter 54 is held tightly in place by a twistable cap 56. A handle 58 is provided on the cap 56 to enable twisting into place. Catch members 60 inwardly extend from the bottom of the housing 12 for abutting with portions of the cap 56 in order to maintain the filter 54 securely in place.

An important aspect of the present invention is that the bottom of housing 12 slopes downwardly toward both filter 48 and filter 50. Specifically, the bottom walls 62 and 64 each slope toward the location of filter 48 in different directions. Thus, condensate or moisture in the left-hand side of the tray of the housing 12 will move by gravity to the filter 48. Likewise, moisture and condensate in the right-hand side of the housing 12 will move by gravity along the similarly sloping housing bottom wall to filter 50.

Referring again to FIG. 2, tray 66 includes apertures 24 as previously noted. An important aspect of the present invention is that the tray bottom is domed at locations 66 between each aperture 24. This domed configuration causes condensate, steam and the like to run into the apertures 24 and prevents the accumulation of droplets of condensate or liquid on the bottom of the tray 16.

Referring to FIG. 3, which illustrates a section of one corner of a tray taken along section lines 3—3 in FIG. 2, the domed portions 66 are shown from a top view. It may be see that each one of the domed portions comprises a rectangle with an aperture 24 located at the corner thereof. The domes 66 are formed such that they slope at the corners thereof to an aperture 24. Channels 68 are formed between adjacent apertures 24 to further assist in draining condensate or liquid through the apertures 24.

FIG. 4 illustrates in greater detail the construction of each of the filters 18, 48 and 50. A twistable cap 56 includes four locking flanges 70. The filter 54 is circular in shape and includes a plastic member having plastic cross-members 72 which support the filter media 74. The filter media may be any suitable type of commercially available filter which allows the passage of air or other sterilizing gases therethrough but which prevents the passage of contaminants such as bacteria. A tab 76 extends from the filter to enable manual insertion and removal of the filter. Filter 54 is disposable such that the filters may be periodically replaced. Four locking members 60 are formed around the recessed area for receiving the filter 54 and the twistable cap 56. Apertures 52 extend through the bottom to enable steam or condensate to pass therethrough.

In operation, the filter 54 is placed within the recessed area and the cap 56 is twisted such that the locking flanges 70 are tightly held within the locking members 60. The cap 56 thus very tightly presses the filter 54 against the side walls of the housing to seal the filter and prevent the passage of air past the edges thereof.

In the preferred embodiment, the present container is formed from a suitable plastic or polymer. As previously noted, clear or translucent plastic has a low thermal conductivity and cannot thus absorb enough radiant heat to eliminate condensate within the housing during the drying cycle of a sterilizer system in an economical time frame. Subsequently, the present invention contemplates the use of additional high thermal conductivity materials in conjunction with clear plastic or polymer in order to cause the absorption of sufficient radiant heat and rapidly radiate that heat through the container to eliminate condensate in an economical time frame such as within twenty (20) minutes. In the preferred embodiment, the present invention contemplates the mixture of high thermal conductivity materials (78), shown in FIG. 5, within the clear or translucent plastic. Alternatively, the invention contemplates the addition of a coating of high thermal conductivity materials to the clear or translucent plastic. It will be understood that various types of high thermal conductivity materials may be utilized to accomplish the object of the present invention. The following are examples which have been found to work well in practice and which provide a sterilization container having a resultant high thermal conductivity which tends to eliminate the formation of condensate therein when used in an autoclave.

EXAMPLE 1

A plastic is formed for use in a conventional plastic forming machine to provide the present container by charging a non-fluxing type high intensity mixer with polypropylene copolymer, calcium carbonate and low molecular weight polyethylene and mixing to 105° C. Aluminum flakes are then added and mixed for 15 to 20 seconds. The mixture is then fed to a single screw compounding extruder and is melt mixed at a temperature of 190° to 205° C. The resulting polymer is then pelletized as it comes out of the extruder. The resulting copolymer pellets may be utilized in a conventional forming machine to form the present container. The formula for use with this example is listed below as a percentage by weight:

| Polypropylene Copolymer | 55-65% approximately |
|---|---|
| Aluminum Flake | 35-50% approximately |
| Low Molecular Weight Polyethylene | 1-5% approximately |
| Calcium Carbonate (CaCO3) | 0-15% approximately |

The polypropylene copolymer may comprise, for example the copolymer manufactured by Eastman Company and noted as Tenite. Aluminum flakes may comprise the aluminum flakes manufactured by Transmet Corporation and identified as K-151. Suitable low molecular weight polyethylene is manufactured by Allied Fibers and Plastics Company as AC-9. A suitable source of calcium carbonate is Thompson, Wyman and Company under the trade name Atomite.

EXAMPLE 2

A non-fluxing type high intensity mixture is charged with polysulfone, EBS, CaCO3 and titanate and is mixed to 150° C. Aluminum flakes are then added and mixed for 15 to 20 seconds. The mixture is then fed to a single screw compounding extruder and is melt mixed to a stock temperature of 250° to 260° C. The formula for this mixture is listed below as a percentage by weight:

| Polysulfone | 50-60% approximately |
|---|---|
| Aluminum Flake w/silane surface treatment | 25-40% approximately |
| (EBS) Ethylenebisstearamide | 1-5% approximately |
| Necalkoxy Titanate | .01-.1% approximately |
| Calcium Carbonate (CaCO3) | 0-15% approximately |

The polysulfone may comprise, for example, polysulfone manufactured by Union Carbide as Udell T-1700. A suitable neoalkoxy titanate is manufactured by Kenrich Petrochemicals under the trade name Capow 38/M.

EXAMPLE 3

A non-fluxing type high intensity mixture is charged with Polysulfone, titanate and EBS and mixed to 150° C. Carbon fiber (80), shown in FIG. 6, is added and the mixture is mixed to 160° C. The mixture is then fed to a single screw compounding extruder and is melt mixed at a stock temperature of 250° to 260° C.

The formula for this mixture is set forth below as a percentage by weight:

| Polysulfone | 90% approximately |
|---|---|
| Carbon Fiber | 10% approximately |
| Neoalkoxy Titanate | .01-.1% approximately |
| (EBS) Ethylenebisstearamide | 1-5% approximately |

The carbon fiber may comprise, for example, the fiber manufactured by Union Carbide Specialty Polymers and denoted as Thornel (VMD).

EXAMPLE 4

A clear or translucent plastic container is formed by one of the mixtures noted above such as polypropylene, calcium carbonate and low molecular weight polyethylene. A container is formed by conventional forming techniques and the interior of the housing and lid is then coated with semi-opaque high thermal conductivity material (82) shown in FIG. 7 such as a heat resistant paint or the like which contains carbon or the like. The container may be coated by painting, dipping or other well-known coating techniques. The clear plastic container may alternatively be impregnated with carbon pigments under pressure.

Sterilization containers formed by any of the above examples will have a relatively high thermal conductivity. For example, the thermal conductivity of polysulfone plastic is approximately 1.7 BTU/HR/F$^2$/° F./IN, while the thermal conductivity of aluminum is 10.8 and carbon fibers 60 BTU/HR/F$^2$/° F./IN. Plastic containers formed in accordance with the present invention absorb substantially more heat through conduction and radiation and, therefore, heat faster and are more effective in moisture evaporation as well as more effective in killing bacteria in marginally operating steam sterilizers. The present container also enables the heat to more rapidly be transmitted to the entire interior, including the tray 16, thereby more effectively treating moisture or bacteria. The present construction of the container with the sloping bottom walls and domed portion of the removable tray also assists in preventing the accumulation of moisture and condensation. It will thus be seen that the present container provides a very efficient technique for sterilizing medical instruments and yet may be made in an economical manner.

Whereas the present embodiment has been described in detail, it should be understood that various changes, alterations and substitutions can be made therein without departing from the spirit and scope of the invention as defined by the appended claims.

What is claimed is:

1. A sterilization container for use in connection with the sterilization of medical instruments, said sterilization container comprising:
   a tray for supporting medical instruments;
   a housing having a bottom and side walls for receiving said tray;
   a lid having edges and a raised portion spaced from said edges, said lid adapted to form a sealing arrangement with said housing;
   an aperture through said raised portion of said lid;
   a first filter, disposed in said aperture, for allowing the passage of sterilizing gases therethrough while preventing the passage of contaminants;
   said housing bottom sloping to at least one location, said location having an opening to drain said condensate from said housing, said opening being laterally spaced from said aperture, when said lid is sealed over said housing, such that an axis of said aperture is spaced apart from said opening; and
   a second filter, disposed in said opening, for passing said condensate and said gases therethrough but inhibiting passage of said contaminants into said housing.

2. The sterilization container of claim 1, wherein said aperture is centrally located in said lid.

3. The sterilization container of claim 1, wherein said housing further comprises pedestals to elevate said housing.